Sept. 14, 1937. W. L. PLANTZ Plant Pat. 262
PEACH
Filed Dec. 29, 1936
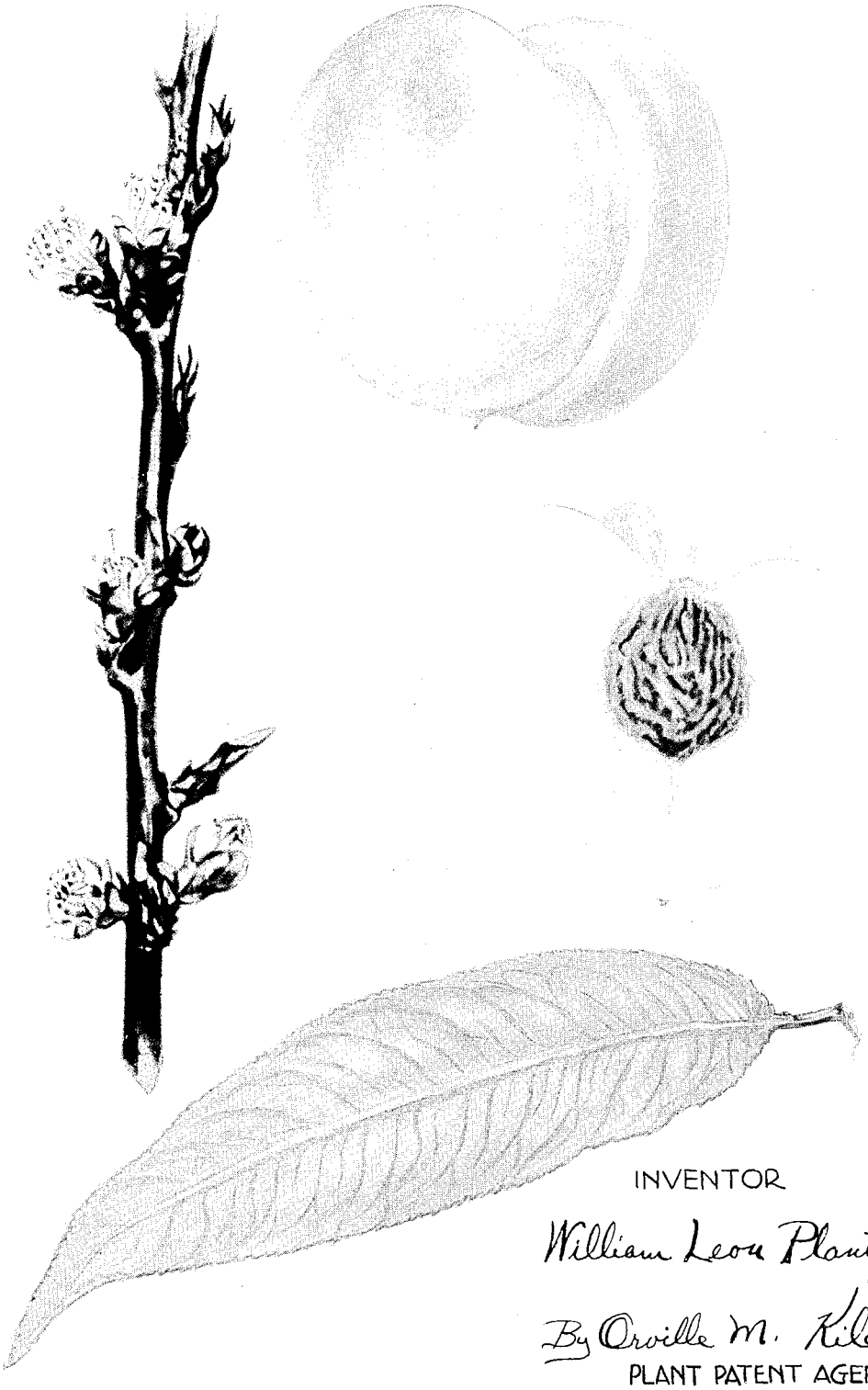
INVENTOR
William Leon Plantz
By Orville M. Kile
PLANT PATENT AGENT Patented Sept. 14, 1937

Plant Pat. 262

UNITED STATES PATENT OFFICE

262

PEACH

William Leon Plantz, near Marysville, Calif.

Application December 29, 1936, Serial No. 118,150

1 Claim. (Cl. 47—62)

My discovery relates to improvements in yellow-fleshed cling peaches of the type used by commercial canners. The tree originated as a seedling, thereafter growing as a root sprout from the understock where a Phillips Cling graft had died. This discovery was made on my own property near Marysville, California.

My new peach is of especial commercial value due to the fact that it offers a peach of fine canning quality and desirable growth habits which ripens at the same time as the Phillips Cling and may be used as a substitute for this variety.

The accompanying illustrations show a whole peach, a cross section of a peach showing the seed, and a branch of blossoms, all in full color, together with a leaf showing shape and size but not true color. The branch of blossoms is slightly enlarged in the original illustrations but fruit and leaf are approximately natural size.

Following is a more detailed description of this new peach and color plate references are to Ridgway's Color Standards and Nomenclature.

*The tree*

The tree is slightly weeping and of average vigor; shaped much like the Guam variety. Main branches stocky and of medium smoothness. Stems a combination of brown and green.

*Foliage:—*

*Leaves.*—Large, averaging 6½ inches long by 1¾ inches wide; lanceolate, with acute points; glossy at stem end; curl slightly backward upon midrib; petiole short and thick.

*Blossoms*

*Flower buds.*—Hardy; small; pubescent.

*Flowers.*—Small.

*Petals.*—Very short.

*Color.*—Deep Rose Pink with edging of Tyrian Pink (Plate XII).

*Stamens.*—Many; large; long filaments.

*Date of bloom.*—From February 26 to March 9 in the vicinity of Marysville, California.

*Fruit*

*Size.*—Large, 3 to 3¾ inches in transverse diameter and 2½ to 2¾ inches in axial diameter.

*Weight.*—Eight to nine ounces.

*Shape.*—Oblate spheroid, slightly irregular and bulged on one side. Small, sharp apex extends beyond regular curve. Suture shallow but flanked on one side by a ridge of considerable size.

*Cavity.*—Deep; regular.

*Skin.*—Tough; with apricot yellow color and red blush at top; tenacious; lightly pubescent.

*Flesh.*—Firm; meaty; juicy; clear rich yellow with no red at the pit; fine texture; few fibers; no gum.

*Flavor.*—Sub-acid; delicate.

*Stone.*—Small, averaging 1⅛ inch wide by 1¼ inch long; plump; clings to flesh over entire surface; apex sharp-pointed; not subject to splitting.

*Ripening period.*—Ripens identically with Phillips Cling (early September).

*Use.*—Used essentially for canning and is a substitute for the Phillips Cling.

It is distinctly understood that the above described characteristics are subject to variation because of differences in soil and climatic conditions.

Having thus disclosed my discovery, I claim:

The new and distinct variety of peach tree herein shown and described, characterized particularly by its slightly drooping form and long foliage; its fruit which ripens at the same time as the Phillips Cling, having firm, oxidation-resisting flesh desirable for canning purposes, also being free from gumming, splitting of pit, and reddening at the pit.

WILLIAM LEON PLANTZ.